United States Patent [19]

Brooks et al.

[11] Patent Number: 5,753,517
[45] Date of Patent: May 19, 1998

[54] QUANTITATIVE IMMUNOCHROMATOGRAPHIC ASSAYS

[75] Inventors: Donald Elliott Brooks; Dana Devine, both of Vancouver, Canada

[73] Assignee: University of British Columbia, Vancouver, Canada

[21] Appl. No.: 625,048

[22] Filed: Mar. 29, 1996

[51] Int. Cl.$^6$ .............. G01N 35/558; G01N 33/546; G01N 33/53
[52] U.S. Cl. .............. 436/514; 436/534; 435/7.1; 422/61
[58] Field of Search .............. 436/514, 534; 435/7.1; 422/61

[56] References Cited

U.S. PATENT DOCUMENTS

| | | | |
|---|---|---|---|
| 4,313,734 | 2/1982 | Leuvering | 23/230 B |
| 4,610,960 | 9/1986 | Mosher | 435/7 |
| 4,690,907 | 9/1987 | Hibino et al. | 436/514 |
| 4,703,017 | 10/1987 | Campbell et al. | 436/501 |
| 4,855,240 | 8/1989 | Rosenstein et al. | 436/514 |
| 4,868,131 | 9/1989 | Hiratsuka | 436/528 |
| 4,975,366 | 12/1990 | Sudo et al. | 435/7 |
| 5,030,558 | 7/1991 | Litman et al. | 435/7.91 |
| 5,039,607 | 8/1991 | Skold et al. | 435/7.5 |
| 5,096,837 | 3/1992 | Fan et al. | 436/514 |
| 5,156,952 | 10/1992 | Litman et al. | 435/7.91 |
| 5,164,294 | 11/1992 | Skold et al. | 435/7.5 |
| 5,232,835 | 8/1993 | Litman et al. | 435/7.93 |
| 5,238,652 | 8/1993 | Sun et al. | 422/61 |
| 5,248,619 | 9/1993 | Skold et al. | 436/514 |
| 5,266,497 | 11/1993 | Imai et al. | 436/514 |
| 5,275,785 | 1/1994 | May et al. | 422/56 |
| 5,334,513 | 8/1994 | Skold et al. | 435/7.92 |
| 5,385,847 | 1/1995 | Yip et al. | 436/534 |
| 5,401,667 | 3/1995 | Koike | 436/514 |
| 5,434,051 | 7/1995 | Allard et al. | 435/7.4 |
| 5,451,507 | 9/1995 | Skold et al. | 435/7.92 |
| 5,468,647 | 11/1995 | Skold et al. | 436/514 |

FOREIGN PATENT DOCUMENTS

| | | |
|---|---|---|
| 0 271 204 A2 | 6/1988 | European Pat. Off. |
| 0 274 198 B1 | 7/1988 | European Pat. Off. |
| 0 284 232 B1 | 9/1988 | European Pat. Off. |
| 0 447 154 A2 | 9/1991 | European Pat. Off. |
| 0 451 686 A2 | 10/1991 | European Pat. Off. |
| 0 466 170 A2 | 1/1992 | European Pat. Off. |
| 0582231A1 | 2/1994 | European Pat. Off. |
| 0585914A2 | 3/1994 | European Pat. Off. |
| 2 204 398 | 11/1988 | United Kingdom . |
| WO 85/05687 | 12/1985 | WIPO . |
| WO 87/07386 | 12/1987 | WIPO . |
| WO 88/01744 | 3/1988 | WIPO . |
| 88/08534 | 11/1988 | WIPO ............ G01N 33/543 |
| WO 92/22797 | 12/1992 | WIPO . |
| WO 93/18067 | 9/1993 | WIPO . |
| WO 94/29696 | 12/1994 | WIPO . |
| WO 95/06240 | 3/1995 | WIPO . |
| WO 95/34815 | 12/1995 | WIPO . |
| WO 97/09620 | 3/1997 | WIPO . |

OTHER PUBLICATIONS

Reeves, S.G. and Durst, R.A., "Novel Optical Measurement Approach for the Quantitation of Liposome Immunomigration Assays", *Analytical Letters*, 28(13):2347–2362 (1995).

Melarnies, Liisa et al., "Evaluation of a Quantitative Photometric Latex Agglutination Immunoassay for α–Foetoprotein," *J. Clin. Chem. Clin. Biochem.* 25:173–176 (1987).

Abe, Junichi et al., "Rapid quantitation of serum myoglobin by latex agglutination turbidimetry," *Clinica Chimica Acta* 203:95–96 (1991).

Borque, Luis et al., "Automated Quantitative Nephelometric Latex Immunoassay for Determining Ferritin in Human Serum," *J. of Clin. Chem. Clin. Biochem.* 6:239–244 (1992).

Roberts, Matthew A. and Durst, Richard A., "Investigation of Liposome–Based Immunomigration Sensors for the Detection of Polychlorinated Biphenyls," *Anal. Chem.* 67:482–491 (1995).

Siebert, Sui Ti A. et al., "Liposome Immunomigration field assay device for Alachlor determination," *Anal. Chim. Acta* 282:297–305 (1993).

Siebert, Sui Ti A. et al., "Improved liposome Immunomigration strip assay for alachlor determination," *Anal. Chim. Acta* 311:309–318 (1995).

Schlfreen, Richard S. et al., "A Quantitative Automated Immunoassay for Fibrinogen/Fibrin Degradation Products," *Clin. Chem.* 31(9):1468–1473 (1985).

Laitinen, Mika P.A. and Vuento, Matti, "Immunochromatographic Assay for Quantitation of Milk Progesterone," *Acta Chemka Scandinaavica* 50:141–145 (1996).

Abe, et al.: Rapid quantitation of serum myoglobin by latex agglutination turbidimetry: Clinica Chinica Acta: 203: pp. 95–95, 1991.

*Primary Examiner*—Ponnathapura Achutamurthy
*Assistant Examiner*—Brett L. Nelson
*Attorney, Agent, or Firm*—Hamilton, Brook, Smith & Reynolds, P.C.

[57] ABSTRACT

Quantitative immunochromatographic assays for measuring the amount of an analyte, and an apparatus for use in the assays, are disclosed. The assays involve obtaining a fluid sample which contains the analyte; supplying a RAMP™ apparatus which includes a membrane having an application point, a detection zone, and a contact region, where the contact region is between the application point and the detection zone, and has antibody-coated particles imbedded within it; contacting the application point with the fluid sample; maintaining the RAMP™ apparatus under conditions sufficient to allow fluid to transport analyte by capillary action to the contact region, where the analyte binds to the antibody-coated particles; further maintaining the apparatus under conditions sufficient to allow fluid to transport analyte-bound antibody-coated particles to the detection zone, where they interact with a detection reagent; and detecting the amount of analyte-bound antibody-coated particles which have reacted with the detection reagent. Alternatively, the fluid sample can be contacted with the detection zone of the apparatus, and the antibody-coated particles are mobilized by addition of fluid to the application point. The RAMP™ apparatus can additionally include one or more of the following features: a wicking pad; an application pad covering the application point; a contact pad covering the contact region; a separator pad between the membrane and the contact pad; and an internal control.

21 Claims, 5 Drawing Sheets

QUANTITATIVE IMMUNOCHROMATOGRAPHIC ASSAYS

BACKGROUND OF THE INVENTION

Quantitative analysis of cells and analytes in fluid samples, particularly bodily fluid samples, often provides critical diagnostic and treatment information for physicians and patients. For example, in a wide variety of clinical and therapeutic situations, blood platelet counts are routinely assessed; abnormalities in platelet counts can cause significant bleeding problems in a patient, and may indicate a multitude of underlying conditions. The early diagnosis of myocardial infarction is aided by quantification of myoglobin in a blood sample, as myoglobin is the earliest marker of cardiac damage (Mair, J. et al., *Br. Heart J.* 68:462–468 (1992)). Renal function and degree of kidney damage can be assessed by analyzing urine for the presence of proteinuria via urinary albumin measurement. Immunological testing methods (Kennedy, D. M. and S. J. Challacombe, eds., ELISA and Other Solid Phase Immunoassays: Theoretical and Practical Aspects, John Wiley and Sons, Chichester (1988)), which take advantage of the high specificity of the antigen-antibody reaction, provide one approach to measurement of analytes. Immunoassays which provide a quantitative measurement of the amount of an analyte in a sample use complex, multi-step procedures and expensive analyzers available only in a laboratory setting. Immunochromatographic assays, such as those described in GB 2,204,398A; U.S. Pat. Nos. 5,096,837, 5,238,652, and 5,266,497; Birnbaum, S. et al., *Analytical Biochem.* 206:168–171 (1992); Roberts, M. A. and R. A. Durst, *Analytical Chem.* 67:482–491 (1995); and Klimov, A. D. et al., *Clinical Chem.* 41:1360 (1995), are simpler, yet do not provide a quantitative measurement of an analyte. Instead, these immunochromatographic assays detect the presence (or absence) of an analyte above a defined cutoff level for the test performed. Thus, there is a need for a general method that can provide a rapid, quantitative measurement of the amount of an analyte present in a sample, and that is sufficiently simple to carry out without use of a laboratory or an individual trained in chemical analysis.

SUMMARY OF THE INVENTION

The invention relates to methods of measuring the amount of an analyte of interest in a fluid sample, using a quantitative immunochromatographic assay; and an apparatus for use in the assay. The assay utilizes a rapid antigen measurement platform (RAMP™) apparatus. The apparatus includes a membrane strip made of a suitable material, such as cellulose nitrate or glass fiber, which has sufficient porosity and the ability to be wet by the fluid containing the analyte, and which allows movement of particles by capillary action. The membrane strip has an application point, a contact region, and a detection zone; the contact region is between the application point and the detection zone. Imbedded in the contact region is a population of particles, such as colloidal metal particles, organic molecules, liposomes, or organic polymer latex particles. The particles are coated with an antibody to the analyte of interest. The particles can be labelled, using a colorimetric, fluorescent, luminescent, or other appropriate label, to facilitate detection. A detection reagent is immobilized in the detection zone. The detection reagent can be antibody to the analyte of interest, or can be the analyte of interest itself. The apparatus can also include one or more of the following features: an application pad, which rests on and covers the application point; a contact pad, which rests on and covers the contact region, and which may have antibody-coated particles imbedded within it; if a contact pad is present, a separator pad, which rests on the membrane in between the contact region and the contact pad; a wicking pad, which rests on the membrane adjacent to the detection zone, such that the detection zone is between the wicking pad and the contact region; and an internal control, which includes internal control particles imbedded in the contact region, a control detection reagent, and a control reaction zone.

To conduct the assay, the application point of the membrane strip is contacted with the fluid sample to be assayed for the analyte of interest. The apparatus is then maintained under conditions which are sufficient to allow capillary action of fluid to transport the analyte of interest, if analyte is present in the sample, through the membrane strip to the contact region. The apparatus is further maintained under appropriate conditions so that when analyte of interest reaches the contact region, the analyte binds to the antibody-coated particles imbedded in the contact region. Antibody-coated particles, including those which are bound with analyte, are mobilized by fluid and move by capillary action through the strip to the detection zone. The detection reagent interacts with analyte-bound antibody-coated particles; interaction of the detection reagent and the analyte-bound antibody-coated particles results in arrest of analyte-bound antibody-coated particles in the detection zone. The amount of analyte-bound antibody-coated particles that are arrested in the detection zone is then detected. The amount of analyte of interest in the fluid sample is related to the amount of analyte-bound antibody-coated particles that are arrested in the detection zone: if the detection reagent is the analyte of interest, the amount of analyte in the fluid sample is inversely related; if the detection reagent is antibody to the analyte of interest, the amount of analyte in the fluid sample is directly related. The amount of analyte is determined from a standard curve for the analyte of interest.

In an alternative immunochromatographic assay, the fluid sample to be assayed for the analyte of interest is applied directly to the detection zone of the apparatus. In this embodiment, the detection reagent is antibody to the analyte of interest. The apparatus is maintained under appropriate conditions so that analyte in the fluid sample interacts with the detection reagent, and is immobilized in the detection zone. Water or an appropriate buffer is then added to the application point of the membrane, to mobilize the antibody-coated particles, which are moved by capillary action into the detection zone. The apparatus is further maintained under conditions which allow interaction of the antibody-coated particles with analyte that is immobilized in the detection zone. Interaction of the antibody-coated particles with immobilized analyte arrests movement of the antibody-coated particles. The amount of analyte in the fluid sample is related to the amount of antibody-coated particles that are arrested in the detection zone, and is determined from a standard curve, as described above.

In a preferred embodiment of the invention, the analyte of interest is thrombospondin, and the fluid sample is a whole blood sample or a platelet-rich plasma sample. Measurement of the thrombospondin concentration in clotted whole blood, or platelet-rich plasma sample, provides a measure of the platelet count in the original blood sample. This parameter is a critical measure of the ability of an individual to maintain normal hemostasis and is followed in a wide variety of clinical settings, including in patients undergoing chemotherapy or patients with platelet destructive disorders or abnormalities of platelet production.

In another preferred embodiment, the analyte of interest is myoglobin, and the fluid sample is a whole blood sample. The concentration of myoglobin and its time dependence is of diagnostic importance in the early assessment of cardiac damage in suspected myocardial infarction.

In yet another preferred embodiment, the analyte of interest is urinary albumin, and the fluid sample is a urine sample. The concentration of urinary albumin is a measure of proteinuria and kidney damage, so the degree of renal dysfunction and its time course can be assessed through the quantitative measurement of albumin levels in urine.

The assays of the current invention are simple, rapid, and usually require addition of no reagents other than a fluid sample containing the analyte, or, in one embodiment, a sample containing the analyte and a buffer solution. The assays can be performed at the point of care of a patient, and do not require skilled technical labor to perform. Furthermore, the apparatus used in the assays is common to all analytes, thus facilitating use of the assays for a wide variety of analytes. Quantification of a wide variety of immunogenic analytes can be performed with the assays.

DETAILED DESCRIPTION OF THE INVENTION

The current invention pertains to methods of quantitatively measuring the amount of an analyte using immunochromatographic assays, apparatus useful in the methods, and kits including the apparatus. As described herein, Applicants have developed a sensitive immunochromatographic assay to measure the level of a soluble, immunogenic analyte in solution.

The term, "analyte," as used herein, refers to the molecule or compound for which the amount will be measured. Examples of analytes include proteins, such as hormones or enzymes; glycoproteins; peptides; small molecules; polysaccharides; antibodies; nucleic acids; drugs; toxins; viruses or virus particles; portions of a cell wall; and other compounds. The analyte is "immunogenic," which indicates that antibodies (as described below) can be raised to the analyte. In preferred embodiments, the analyte is thrombospondin, myoglobin, or urinary albumin.

Figure 1:
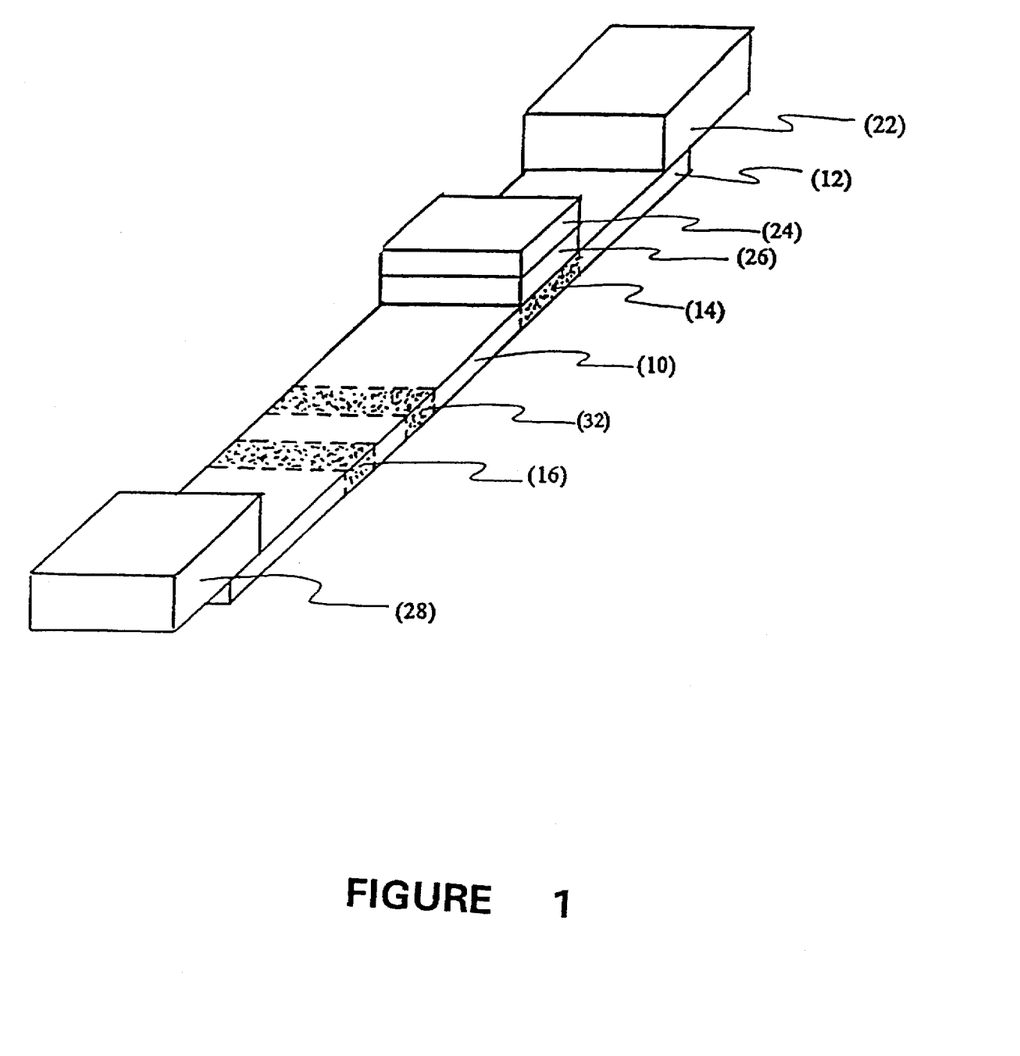
FIG. 1 is a depiction of the Rapid Antigen Measurement Platform (RAMP™) apparatus.

To conduct the immunochromatographic assays of the current invention, a rapid antigen measurement platform (RAMP™) apparatus is used. FIG. 1 depicts the RAMP™ apparatus. The RAMP™ apparatus includes: a membrane strip (10) having an application point (12), a contact region (14), and a detection zone (16). The membrane strip can be made of a substance having the following characteristics: sufficient porosity to allow capillary action of fluid along its surface and through its interior; the ability to allow movement of antibody-coated particles by capillary action (i.e., it must not block the particles); and the ability to be wet by the fluid containing the analyte (e.g., hydrophilicity for aqueous fluids, hydrophobicity for organic solvents). Hydrophobicity of a membrane can be altered to render the membrane hydrophilic for use with aqueous fluid, by processes such as those described in U.S. Pat. No. 4,340,482, or U.S. Pat. No. 4,618,533, which describe transformation of a hydrophobic surface into a hydrophilic surface. Examples of membrane substances include: cellulose, cellulose nitrate, cellulose acetate, glass fiber, nylon, polyelectrolyte ion exchange membrane, acrylic copolymer/nylon, and polyethersulfone. In a preferred embodiment, the membrane strip is made of cellulose nitrate.

The "application point" (12), as used herein, is the position on the membrane where the fluid sample is applied. The RAMP™ apparatus can optionally include an "application pad" (22) which rests on the membrane, covering the application point. The application pad can be made of an absorbent substance which can deliver a fluid sample, when applied to the pad, to the application point on the membrane. Representative substances include cellulose or glass fibers.

The "contact region" of the membrane is adjacent to the application point. The RAMP™ apparatus can optionally include an "contact pad" (24) which rests on the membrane, covering the contact region. The contact pad can be made of an absorbent substance; representative substances include cellulose, cellulose nitrate, cellulose acetate, glass fiber, nylon, polyelectrolyte ion exchange membrane, acrylic copolymer/nylon, and polyethersulfone. If a contact pad is present, the RAMPS apparatus can also optionally include a "separator pad" (26) which rests on the membrane, between the contact region and the contact pad. The separator pad can be made of an absorbent substance; representative substances include cellulose, cellulose nitrate, cellulose acetate, glass fiber, nylon, polyelectrolyte ion exchange membrane, acrylic copolymer/nylon, and polyethersulfone. In a preferred embodiment, if a separator pad and a contact pad are both present, they are made of the same substance.

Imbedded in the "contact region" of the membrane, and/or in the contact pad if it is present, is a population of particles which are coated with antibodies (or other types of molecules that specifically bind) to the analyte of interest. The population of particles varies, depending on the size and composition of the particles, the composition of the membrane, and the level of sensitivity of the assay. The population typically ranges approximately between $4 \times 10^6$ and $4 \times 10^9$ particles, although fewer than $4 \times 10^6$ particles can be used. In a preferred embodiment, the population is approximately $4 \times 10^8$ particles.

The particles imbedded in the contact region are particles which can be coated with antibodies or with other agents that specifically bind to the analyte. Examples of substances include colloidal gold particles; colloidal sulphur particles; colloidal selenium particles; colloidal barium sulfate particles; colloidal iron sulfate particles; metal iodate particles; silver halide particles; silica particles; colloidal metal (hydrous) oxide particles; colloidal metal sulfide particles;

colloidal lead selenide particles; colloidal cadmium selenide particles; colloidal metal phosphate particles; colloidal metal ferrite particles; any of the above-mentioned colloidal particles coated with organic or inorganic layers; protein or peptide molecules; liposomes; or organic polymer latex particles. In a preferred embodiment, the particles are polystyrene latex beads, and particularly, polystyrene latex beads that have been prepared in the absence of surfactant, such as surfactant-free Superactive Uniform Aldehyde/Sulfate Latexes (Interfacial Dynamics Corp., Portland, Oreg.). The size of the particles is related to porosity of the membrane: the particles must be sufficiently small to be transported along the membrane by capillary action of fluid.

The particles can be labelled to facilitate detection. Examples of labels include luminescent labels; colorimetric labels, such as dyes; fluorescent labels; or chemical labels, such as electroactive agents (e.g., ferrocyanide).

The particles are coated with an agent that specifically binds to the analyte of interest. In a preferred embodiment, the particles are coated with antibodies to the analyte of interest. The antibodies can be monoclonal antibodies or polyclonal antibodies. The term "antibody", as used herein, also refers to antibody fragments which are sufficient to bind to the analyte of interest. Alternatively, molecules which specifically bind to the analyte of interest, such as engineered proteins having analyte binding sites, can also be used (Holliger, P. and H. R. Hoogenbloom, *Trends in Biotechnology* 13:7–9 (1995); Chamow, S. M. and A. Ashkenazi, *Trends in Biotechnology* 14:52–60:1996)). In another embodiment, if the analyte of interest is a ligand, a receptor which binds to the ligand can be used. If the analyte is an antibody of known specificity, the particles can be coated with the antigen against which the analyte-antibody is directed.

The contact region of the membrane is between the application point and the "detection zone" (16) of the membrane. The detection zone, as described herein, refers to a point on the membrane strip at which a "detection reagent" is immobilized. In one embodiment, the detection reagent is the analyte of interest. In a second embodiment, the detection reagent is antibody directed against the same epitope of the analyte, or against a different epitope of the analyte, as those antibodies coated onto the particles.

The RAMP™ apparatus can also optionally include a "wicking pad" (28). The term, "wicking pad," as used herein, refers to an absorbent substance which soaks up solution that has been transported by capillary action to the end of the membrane strip. Examples of substances include cellulose and glass fiber.

In order to compensate for variations in membrane properties from assay to assay, the apparatus can additionally include an internal control, which includes internal control particles, a control detection reagent, and a control reaction zone (32). Internal control particles are imbedded in the contact region with the antibody-coated particles. The "internal control particles" are identical to the antibody-coated particles, and are coated with the same surface concentration of an antibody, except the antibody on the internal control particles is directed against a control detection reagent which does not react with the antibody directed against the analyte. The "control detection reagent" can be a reagent which does not interact with either the analyte to be measured, the antibody on the antibody-coated particles, or the detection reagent. In a preferred embodiment, the control detection reagent is Keyhole Limpet Hemocyanin (KLH). The control detection reagent is coated on the membrane in a "control reaction zone" (32). The control reaction zone, as described herein, refers to a point on the membrane strip at which the control detection reagent is immobilized. The control reaction zone can be between the contact region and the detection zone; alternatively, the detection zone can be between the contact region and the control reaction zone.

To perform the quantitative immunochromatographic assay, a fluid sample containing the analyte of interest is obtained. The fluid can be a fluid that wets the membrane material; that supports an antibody/antigen reaction (i.e., does not interfere with antibody/antigen interaction); and that has a viscosity that is sufficiently low to allow movement of the fluid by capillary action. In a preferred embodiment, the fluid is an aqueous solution (such as a bodily fluid).

In a first embodiment of the quantitative assay, the application point of the membrane strip is contacted with the fluid sample containing the analyte of interest. If the apparatus includes an application pad, the fluid sample is applied to the application pad, which delivers the fluid sample to the application point. After the membrane strip is contacted with the fluid sample containing the analyte of interest at the application point, the membrane strip is maintained under conditions which allow fluid to transport the analyte by capillary action to the "contact region" of the membrane.

When the analyte is transported to the contact region, analyte that is present in the fluid binds to the antibody-coated particles imbedded in the contact region. If a contact pad, or a contact pad and a separator pad, are present, the pads facilitate controlled release of antibody-coated particles, and contact with a larger volume of the fluid sample with the antibody-coated particles. "Binding" of analyte to the antibody-coated particle indicates that one or more of the antibodies coated onto the particle are bound to analyte of interest. An antibody-coated particle which is "insufficiently bound" is one at which the binding sites of the antibodies coated onto the particle are not completely filled by the analyte of interest, such that antibody on the particle is capable of binding to additional analyte. An antibody-coated particle which is insufficiently bound to analyte of interest, as described herein, can be bound to some analyte, or to no analyte. If no further analyte can be bound to the antibody-coated particle, the antibody-coated particle is said to be "saturated" with analyte.

Antibody-coated particles which have been maintained under conditions allowing analyte in the fluid to bind to the antibody-coated particles imbedded in the contact region, and/or the contact pad, if present, are referred to herein as "contacted antibody-coated particles". Contacted antibody-coated particles may or may not have analyte bound to the antibodies, depending on whether or not analyte is present in the fluid sample and whether analyte has bound to the antibody on the antibody-coated particles.

Capillary action of the fluid from the fluid sample mobilizes the contacted antibody-coated particles, and moves the contacted antibody-coated particles along the membrane to a "detection zone" on the membrane. The movement of contacted antibody-coated particles is arrested by binding to the detection reagent. If the detection reagent is the analyte of interest, the detection reagent binds to antibody on those contacted antibody-coated particles which are insufficiently bound to analyte of interest. If the detection reagent is antibody to the analyte of interest, the detection reagent binds to analyte which is bound to antibody on the contacted antibody-coated particles. The term, "detection-reagent-particle complexes", as used herein, refers to a complex of the detection reagent and contacted antibody-coated particles. The detection-reagent-particle complexes are arrested (e.g., immobilized) in the detection zone.

The amount of detection-reagent-particle complexes arrested in the detection zone is detected. If the antibody-coated particles have been labelled, the complexes are detected using an appropriate means for the type of label. Alternatively, the amount of detection-reagent-particle complexes is detected by an optical method, such as by measuring the light scattering in the detection zone. The amount of detection-reagent-particle complexes can also be measured using electrical conductivity or dielectric (capacitance). Alternatively, electrochemical detection of released electroactive agents, such as indium, bismuth, gallium or tellurium ions, as described by Hayes et al. (*Analytical Chem.* 66:1860–1865 (1994)) or ferrocyanide as suggested by Roberts and Durst (*Analytical Chem.* 67:482–491 (1995)), can be used. For example, if liposomes are used, ferrocyanide encapsulated within the liposome can be released by addition of a drop of detergent at the detection zone, and the released ferrocyanide detected electrochemically, as outlined by Roberts and Durst. If chelating agent-protein conjugates are used to chelate metal ions, addition of a drop of acid at the detection zone will release the ions and allow their quantitation by anodic stripping voltametry as described by Hayes et al.

The amount of analyte in the fluid sample is then determined, based on the amount of detection-reagent-particle complexes arrested in the detection zone. If the detection reagent is the analyte of interest, the amount of analyte of interest in the fluid sample is inversely related to the amount of detection-reagent-particle complexes arrested in the detection zone. If the detection reagent is the antibody, the amount of analyte of interest in the fluid sample is directly related to the amount of arrested detection-reagent-particle complexes in the detection zone.

The amount of analyte of interest can be determined through the use of a standard curve. The standard curve is generated by preparing a series of control samples, containing known concentrations of the analyte of interest in the fluid in which the analyte is to be detected (such as serum depleted of the analyte). The quantitative immunochromatographic assay is then performed on the series of control samples; the amount of detection-reagent-particle complexes in the detection zone is measured for each control sample; and the amounts are plotted as a function of the concentration of analyte included in the control sample. Samples containing an unknown amount of analyte (the "test samples") are assayed by measuring the amount of detection-reagent-particle complexes for the test sample, and the concentration of analyte in the test sample is determined by referring to the standard curve. One standard curve can be generated and used for all test samples; it is not necessary that the standard curve be regenerated for each test sample. The standard curve is recalibrated for each different detection reagent.

If internal control particles are used in the assay, the internal control particles are mobilized by fluid, and are moved by capillary action to the control reaction zone. The internal control particles bind to the control detection reagent in the control reaction zone, generating internal control particle-control detection reagent complexes (herein referred to as "control complexes"). The amount of control complexes is detected in the same manner as the amount of detection-reagent-particle complexes in the detection zone. The ratio (R) of the amount of detection-reagent-particle complexes to the amount of control complexes present, is used to determine the amount of analyte present, utilizing a standard curve. The standard curve is generated by preparing a series of control samples, containing known concentrations of the analyte of interest in the fluid in which the analyte is to be detected (such as serum depleted of the analyte). The quantitative immunochromatographic assay is then performed on the series of control samples; the value of R is measured for each control sample; and the R values are plotted as a function of the concentration of analyte included in the control sample. Samples containing an unknown amount of analyte (the "test samples") are assayed by measuring the value of R for the test sample, and the concentration of analyte in the test sample is determined by referring to the standard curve. As above, one standard curve can be generated and used for all test samples; it is not necessary that the standard curve be re-generated for each test sample.

In a second embodiment of the invention, the detection zone of the membrane strip, rather than the application point, is contacted with the fluid sample. In this embodiment, the detection reagent is antibody to the analyte of interest. The membrane strip is maintained under conditions which are sufficient to allow analyte of interest in the fluid sample to bind to the antibody in the detection zone, thereby generating immobilized analyte. Subsequently, the application point of the membrane is contacted with water or a buffer. The buffer can be an aqueous fluid that wets the membrane material; that supports an antibody/antigen reaction (i.e., does not interfere with antibody/antigen interaction); and that has a viscosity that is sufficiently low to allow movement of the fluid by capillary action. Examples of buffers include, for example, saline, or 50 mM Tris-HCl, pH 7.4. The buffer transports the population of antibody-coated particles imbedded in the membrane at the contact region and/or contact pad to the detection zone. The membrane strip is further maintained under conditions which are sufficient to allow the immobilized analyte to interact with the antibody-coated particles. Interaction of immobilized analyte with antibody-coated particles arrests the movement of the antibody-coated particles, and generates arrested analyte-particle complexes. The amount of arrested analyte-particle complexes in the detection zone is then measured, as described above, and the amount of analyte in the fluid sample is determined using a standard curve, as described above, and can be determined with or without an internal control. The amount of analyte of interest in the fluid sample is directly related to the amount of arrested analyte-particle complexes in the detection zone.

In a preferred embodiment of the invention, the analyte of interest is thrombospondin, and the fluid sample is a whole blood sample, or a platelet-rich plasma sample derived from whole blood. A platelet-rich plasma sample is isolated from the blood sample, using standard methods. In order to conduct the quantitative assay for thrombospondin using whole blood or a platelet-rich plasma sample, thrombospondin must be released from the platelets, either before application of the sample to the apparatus, or by application of the sample to the apparatus. Thrombospondin can be released from platelets in the whole blood sample or in the platelet-rich plasma sample by methods such as a releasing agent or contact activation. Releasing agents such as thrombin, calcium ionophore A23187, phorbol esters and detergents, can all be used to release thrombospondin from platelets. Alternatively, thrombin generation by the natural clotting process that is initiated by contact activation when blood is drawn into glass containers in the absence of anticoagulant is sufficient for release of thrombospondin. In a preferred embodiment, the RAMP™ apparatus includes an application pad, which is used to release thrombospondin from platelets. The whole blood sample, or the platelet-rich plasma sample is applied to the application pad, and release of the thrombospondin results. The application pad can additionally be impregnated with one or more releasing agent(s), such as those described above, to facilitate release of thrombospondin. The thrombospondin released by the releasing agent or by contact activation is referred to herein as "released thrombospondin." The detection reagent can be thrombospondin, an antibody to thrombospondin, or another suitable agent. The standard curve for thrombospondin can be generated by preparing a series of control samples of known concentrations of thrombospondin in serum containing no detectable thrombospondin. The quantitative immunochromatographic assay is performed on the series of control samples; the amount of detection-reagent-particles complexes in the detection zone is determined for each control sample; and the values are plotted as a function of the concentration of thrombospondin included in the control samples.

The amount of thrombospondin in a sample can be used to determine the platelet count of an individual, based on a relationship between the amount of thrombospondin released from platelets in a sample and the platelet count. A reference curve for the relationship between platelet count and thrombospondin in standard samples can be generated, and the platelet count determined from the amount of thrombospondin in the test samples. Alternatively, a reference curve can be generated by plotting the amount of thrombospondin as a function of platelet concentration in a series of control samples of blood containing a known number of platelets. More detailed teachings concerning the relationship between thrombospondin and platelet count are described in U.S. patent application Ser. No. 08/625,770, entitled "Determination of Platelet Count Employing Assay for Platelet Granule Proteins", filed on Mar. 29, 1996, the entire teachings of which are incorporated herein by reference.

In another preferred embodiment of the invention, the analyte of interest is myoglobin. The sample can be, for example, whole blood, such as anticoagulated whole blood; plasma; or serum. In a preferred embodiment the sample is whole blood. The apparatus preferentially includes an application pad and an internal control (comprising internal control particles, a control detection reagent, and a control reaction zone). Preferentially, myoglobin is used as the detection reagent, and is coated on the membrane in the detection zone. The membrane is blocked with a suitable agent, such as 1% PVA. The quantitative immunochromatographic assay is initiated by adding the fluid sample to the application pad, and the assay is allowed to proceed. The ratio (R) of the amount of myoglobin-antimyoglobin-particle complex in the detection zone to the amount of control complexes in the control reaction zone is used to determine the amount of myoglobin present, using a standard curve. The standard curve is generated by preparing a series of control samples of known concentrations of myoglobin in whole blood, plasma or serum, containing no detectable myoglobin. The quantitative immunochromatographic assay is performed on the series of control samples; the value of R is calculated for each control sample; and the R values are plotted as a function of the concentration of myoglobin included in the control sample.

The analyte of interest is urinary albumin in another preferred embodiment, and the fluid sample is a urine sample. Albumin is used as the detection reagent, and is coated on the membrane in the detection region. The membrane is blocked as described above. The assay is initiated by applying a urine sample to the application pad, and the assay allowed to proceed. The standard curve is generated by performing the quantitative immunochromatographic assay on a series of control samples of urine free of detectable albumin, to which are added known amounts of albumin.

The invention also includes kits which contain the apparatus described herein. Other kit components can include: buffers, fluid collection means, and control samples for generation of a standard curve.

The invention is further illustrated by the following examples, which are not intended to be limiting in any way.

EXAMPLE 1

Quantitative Immunochromatographic Assay for Thrombospondin

Experiments were conducted to facilitate membrane selection and selection of blocking agents; and to examine conditions for latex release and migration, conditions for latex migration arrest, and the dependence of inhibition of latex migration arrest on free analyte concentration.

A. Membrane Selection

A suitable membrane was selected by determining the binding characteristics of the detection reagent to the membrane and the rate of capillary flow through the membrane. The important binding characteristics are the affinity and capacity of the membrane for the detection reagent and the lack of reversibility of binding by buffer, blocking reagents or proteins (such as plasma proteins) present in the fluid sample to be analyzed that might compete for binding sites on the membrane.

1. Equilibrium Binding of Thrombospondin to Membranes

Experiments were conducted to determine the amount of thrombospondin adsorbed to various membranes under equilibrium conditions, and to determine the amount of thrombospondin (fraction) desorbed from membrane surfaces by competition with serum proteins. The membranes used are shown in Table 1.

TABLE 1

Membranes used in Thrombospondin Equilibrium Binding Studies

| Supplier | Membrane Material | Pore Size ($\mu$) | Thickness (cm) | Average Dry Weight (used in expts.) (g) | Geometric "Surface" Area* ($cm^2/g$) |
|---|---|---|---|---|---|
| Sartorius | | | | | |
| NC5 | Nitrocellulose | 5 | 0.014 | 0.00215 | 279.68 |
| NC8 | Nitrocellulose | 8 | 0.014 | 0.0021 | 286.34 |
| Gelman | | | | | |
| NT5000 | Nitrocellulose | 5 | 0.0139 | 0.00195 | 308.37 |
| NF10 | Nitrocellulose | 10 | | 0.0015 | 400.88 |
| A/E | Glass Fibre | 1 | 0.0456 | 0.00423 | 142.16 |
| MSI | | | | | |
| M5 | Nylon | 5 | 0.1 | 0.00325 | 185.02 |
| M10 | Nylon | 10 | 0.1 | 0.00273 | 220.26 |
| S&S | | | | | |
| NC5 | Nitrocellulose | 5 | 0.0139 | 0.0023 | 261.44 |
| NC8 | Nitrocellulose | 8 | 0.0126 | 0.0022 | 273.33 |

*The geometric "surface" area quoted is simply the area of the circular membrane disc, the thickness of the membrane disc was not taken into consideration.

$^{125}$I-thrombospondin was prepared by iodinating 100 µg of thrombospondin with 10 µl of $Na^{125}I$ (0.1 mCi) using Iodobeads (Pierce Chemicals, Rockford, Ill.). Unconjugated $^{125}I$ was removed by gel filtration (Sephadex G-25) and diluted with unlabelled thrombospondin to give a stock 20 ml of approximately 200 µg thrombospondin/ml (specific activity approximately 463 CPM/µg thrombospondin) in Tris-HCl buffer (50 mM, pH 7.4).

Circular membrane discs (0.875 cm in diameter) were obtained by punching holes through the membranes using an arch punch. The average dry weight of each membrane disc was determined by weight in 3 or 4 membrane discs.

Dry membrane discs were soaked in 1 ml solutions containing (i) 20, (ii) 40, (iii) 80, and (iv) 200 µg/ml thrombospondin, made from the stock solution above, and allowed to equilibrate overnight without shaking. The membranes were then transferred to new tubes, and the radioactivity of the membrane and original thrombospondin solution were measured to obtain the equilibrium thrombospondin concentration and the amount of thrombospondin bound on the membranes. The thrombospondin binding capacity of each membranes was determined by Scatchard plots (Cantor, C. R. and P. R. Schimmel, Biophysical Chemistry, Part III. The Behavior of Biological Macromolecules, W. H. Freeman Co., San Francisco (1980), p. 856). A summary of the thrombospondin binding capacity of the membranes is shown in Table 2.

TABLE 2

Summary of Thrombospondin Binding Capacity of Membranes

| Membrane | Saturation binding values of thrombospondin ($\mu g/g$) to membranes | Saturation binding values of thrombospondin ($\mu g/cm^2$)* to membranes |
| --- | --- | --- |
| Sartorius | | |
| NC5 | 2586.5 | 9.25 |
| NC8 | 1954.7 | 6.83 |
| Gelman | | |
| NT5000 | 3712.2 | 12.04 |
| NF10 | 503.0 | 1.25 |
| A/E | 6686.5 | 47.03 |
| MSI | | |
| M5 | 1388.1 | 7.50 |
| M10 | 1370.4 | 6.22 |
| S&S | | |
| NC5 | 1662.0 | 6.36 |
| NC8 | 1236.0 | 4.52 |

*The geometric "surface" area used in estimating the saturation binding values of thrombospondin in ($\mu g/cm^2$) is simply the area of the circular membrane disc, the thickness of the membrane disc was not taken into consideration.

The maximum surface concentration of thrombospondin ($\mu g/g$) shows that the thrombospondin binding capacity of the membranes increase in the order:

A/E>NT5000>NC5>NC8>S&S NC5>M5>M10>S&S NC8>NF10.

Generally, membranes with small effective pore size (1 and 5 μm) bind more thrombospondin per unit weight than those with large effective pore size (8 and 10 μm), except for the NC8 membrane, which appears to bind more thrombospondin than the smaller effective pore size S&S N5 and M5 membranes. This is presumably because there is more fibre material available for adsorption, per unit weight, in the small effective pore size membranes than in the large effective pore size membranes. There is considerable variation in the binding capacity of membranes with similar material, effective pore size, and thickness, as exhibited by the (Sartorius) NC5, (Gelman) NT5000, and the (S&S) NC5.

The reversibility of adsorption was then studies. Membranes were washed with Tris-HCl buffer (50 mM, pH 7.4) by static soaking for 15 minutes and the amount of thrombospondin retained on the membranes was determined by gamma counting. The membranes were subjected to three cycles of wash procedure, counting the radioactivity each time to determine the amount of thrombospondin retained. After the third buffer wash, membranes were incubated in 1 ml of serum for 15 minutes and the amount of thrombospondin retained determined by gamma counting. Exposing the membranes carrying adsorbed thrombospondin to buffer washes two or three times effectively removed unbound thrombospondin within the membrane interstices. Membranes washed in buffer after having thrombospondin adsorbed overnight, did not desorb significantly, when exposed to potentially competing serum proteins (data not shown).

2. Thrombospondin Binding to Membrane by Spot-Wetting

To apply the detection reagent to the detection zone, a solution of detection reagent is sprayed or applied in drops to the detection zone of the membrane (spot wetting). In this process the detection reagent dries onto the membrane surfaces to which it has access, from a solution whose concentration will change as the medium evaporates or migrates by capillarity through the fibers, a process that differs from that which occurs when a large volume of a solution of detection reagent is equilibrated with membrane. In latex immunochromatographic assays, the detection reagent is applied by wetting the target area; the membrane is then blocked with a polymer or detergent. Application of the blocking agent can displace bound detection reagent. Similarly, during the migration phase of the assay, as the wetting front advances up the membrane and reaches the target area, blocking agents can be swept along with the wetting front and displace detection reagent. Therefore, experiments were conducted to determine thrombospondin binding characteristics on membranes under conditions similar to those under which immunochromatographc assays are performed, and to determine membrane capacity to retain bound thrombospondin at the point of application following drying and rehydration by various blocking agents.

Because of its binding properties, the Sartorius NC5 membrane was selected for further study. Membrane (Sartorius NC5) was cut into strips (1.5 cm by 9.0 cm) and divided into six square sections (1.5 cm by 1.5 cm). The size of square was chosen such that a 10 μl solution of thrombospondin would spread on the membrane to just fill the square.

To examine reversal of thrombospondin by blocking agents, 10 μl of radiolabelled thrombospondin was spot blotted on the second square section, near one end of the membrane strip and allowed to dry overnight. The membrane strips were then dipped in 1% w/v blocking agent in Tris-HCl buffer (50 mM, pH 7.4) such that the section with bound thrombospondin was just above the blocking solution, and the blocking solution was allowed to wick to the other end of the membrane. The membrane strips were then dried overnight and cut into sections (1.5 cm by 1.5 cm) and each section counted to determine the amount of thrombospondin retained and/or displaced along the membrane strip by the blocking agent. Results are shown in Table 3.

TABLE 3

Amount of Thrombospondin on Membrane Sections as Percent of Total Amount Immobilized Amount of thrombospondin left on membrane sections after incubation in blocking agent solutions

| Blocking agent | NC5 | NC8 | NT5000 | NF10 | A/E | M5 | M10 | S&S5 | S&S8 |
|---|---|---|---|---|---|---|---|---|---|
| PVA (15,000) | 72 | 76 | 72 | 64 | 72 | 86 | 97 | 61 | 57 |
| PVA (22,000) | 89 | 86 | 74 | 63 | 75 | 94 | 82 | 80 | 71 |
| PVA (49,000) | 68 | 70 | 77 | 48 | 76 | 52 | 65 | 75 | 68 |
| PVP (40,000) | 87 | 82 | 80 | 64 | 61 | 74 | 99 | 83 | 78 |
| PEG (6,000) | 92 | 75 | 72 | 67 | 63 | 78 | 86 | 85 | 77 |
| PEG (20,000) | 88 | 86 | 61 | 82 | 71 | 79 | 88 | 97 | 71 |
| Dextran T500 | 98 | 83 | 94 | 71 | 90 | 86 | 93 | 83 | 78 |
| Pluronic P-105 | 74 | 68 | 67 | 63 | 71 | 79 | 85 | 61 | 51 |
| Triton X-100 | 53 | 70 | 68 | 56 | 67 | 73 | 64 | 49 | 75 |
| Tween 20 | 45 | 65 | 75 | 51 | 67 | 71 | 69 | 40 | 73 |
| BSA | 73 | 79 | 86 | 77 | 62 | 82 | 85 | 67 | 76 |
| Buffer (Tris-HCl) | 88 | 85 | 83 | 77 | 55 | 82 | 83 | 86 | 82 |

In general, most of the water soluble polymers did not displace thrombospondin that has been immobilized and air dried on (NC5) membrane to a great extent. With the exception of PVA (15,000), all the water soluble polymers used as blocking agents displaced thrombospondin, under wicking conditions, to the same extent as Tris-HCl buffer and BSA. Based on the adsorption results, the amount of thrombospondin released by buffer should largely represent the amount of thrombospondin dried into the membrane but not directly associated with membrane fibers. All the neutral detergents (Tween 20 and Triton X-100) and a surfactant copolymer (Pluronic P-105) used as blocking agents displaced thrombospondin, under wicking conditions, to a greater degree than the water soluble polymers, BSA, and Tris-HCl buffer. Nevertheless, even these agents left at least 60% of the applied thrombospondin on target.

To determine how much thrombospondin was removed by blocking agents drying onto membrane and being rehydrated, the membrane strip section, with the thrombospondin spot, was soaked in Tris-HCl buffer for approximately 15 minutes after the blocking agents had wicked up the membrane in the above experiments, and the radioactivity of the strip section and the buffer solution used for re-equilibration were re-counted. Results are shown in Table 4.

TABLE 4

Thrombospondin on (Sartorius) NC5 Membrane Strip As a Percent of Amount on Membrane Strip Section With Thrombospondin Spot

| Blocking agent | % thrombospondin |
|---|---|
| PVA (15,000) | 93 |
| PVA (22,000) | 94 |
| PVA (49,000) | 90 |
| PVP (40,000) | 92 |
| PEG (6,000) | 96 |
| PEG (20,000) | 95 |
| Dextran T500 | 95 |
| Pluronic P-105 | 94 |
| Triton X-100 | 94 |
| Tween 20 | 93 |
| BSA | 97 |
| Buffer (Tris-HCl) | 96 |

Subsequent washing in buffer released little further thrombospondin, indicating that dried-on blocking agents, when wetted, did not significantly displace thrombospondin already associated with the membrane.

3. Rate of Capillary Flow of Buffer and Serum Through Membranes

Experiments were conducted to determine the migration rate of buffer and serum along a specified length of membrane. Membranes enumerated in Table 1 were cut into strips (1.0 cm by 6.0 cm) and divided into six sections (1.0 cm by 1.0 cm). Each membrane strip was placed vertically in a tube with the bottom of each strip immersed in buffer (Tris-HCl, 50 mM, pH 7.4) or fresh human serum. After allowing the fluid front to migrate 2 cm, the time required for the fluid migration through each subsequent cm was recorded. Results are shown in Table 5.

TABLE 5

Summary of Buffer and Serum Migration Rates in Membranes

| Membrane | Time for buffer to migrate 4 cm along membrane (minutes) | Time for serum to migrate 4 cm along membrane (minutes) |
|---|---|---|
| Sartorius | | |
| NC5 | 3.97 | 5.17 |
| NC8 | 3.17 | 3.27 |
| Gelman | | |
| NT5000 | 5.47 | 9.20 |
| NF10 | 3.40 | 3.87 |
| A/E | 1.60 | 3.27 |
| MSI | | |
| M5 | 5.40 | 11.50 |
| M10 | 2.53 | 3.70 |
| S&S | | |
| NC5 | 3.53 | 7.33 |
| NC8 | 3.87 | 2.98 |

Except for the NT5000 membrane, Tris buffer (50 mM, pH 7.4) showed similar flow rate (3–4 minutes/4 cm) for all the nitrocellulose membranes (NC5, NC8, NF10, S&S NC5, and S&S NC8) with no clear difference in the flow rate with respect to effective pore sizes, except for the NT5000 which was significantly slower. The effect of effective pore size was more pronounced in the flow rate of serum: membranes with larger effective pore sizes (8–10 μm) showed similar flow rate as in buffer, while membranes with smaller effective pore sizes (1–5 μm) showed a much reduced flow rate in serum than in buffer. Sartorius NC5 provided the fastest serum flow for the smaller effective pore size membranes.

B. Selection of Membrane Blocking Agents

Methods for "blocking" the membrane so that antibody-coated latex would not adhere to the membrane in the presence of serum proteins were investigated.

1. Equilibrium Binding of IgG to Membranes

Experiments were conducted to determine the amount of IgG adsorbed to various membranes under equilibrium conditions, and to determine the amount of IgG retained on surfaces after wash cycle with buffer and blocking agent. Dry membrane discs (diameter=0.875 cm) were soaked in 2 ml solutions containing (a) 5, (b) 10, (c) 25, (d) 50, (e) 100, and (f) 200 μg/ml of radiolabelled IgG, and allowed to equilibrate overnight, at room temperature, without shaking. The membranes were then transferred to new tubes and the radioactivity of the membranes and IgG solution measured to obtain the equilibrium IgG concentration, and the amount bound on the membranes. Membranes were then washed in tris-HCl buffer (50 mM, pH 7.4) by static soaking for 15 minutes and the amount of IgG retained on the membranes was determined by gamma counting. The membranes were then subjected to another cycle of buffer wash, and 1% PVA (average molecular weight=15,000) solution in tris-HCl buffer (50 mM, pH 7.4).

Re-equilibriating the membranes bearing adsorbed IgG in fresh buffer two times appeared to remove most of the unbound IgG within the membrane interstices. The solution of 1% PVA (15,000) displaced a considerable amount of IgG bound to the nitrocellulose membranes, whereas for the glass fibre and nylon membranes, it did not appear to remove as much bound IgG (data not shown), suggesting that PVA (15,000) would probably be a better blocking agent for the nitrocellulose membranes than for the glass fibre and the nylon membranes.

2. IgG Binding to Membranes by Spot-Wetting

Experiments were conducted to determine IgG binding characteristics under conditions similar to those under which immunochromatographic assays are performed, and to determine the amount of IgG retained on membranes after incubating in blocking agent solution and serum.

Dry membranes were cut in square sections (1.5 cm by 1.5 cm) and 10 μl of radiolabelled IgG was spot blotted on each membrane section and allowed to air-dry for 3 hours. The amount of IgG immobilized on the membrane strips was determined by gamma counting. Air-dried membrane sections were first incubated in (2 ml) solution of 1% PVA (15,000) in tris-HCl buffer for 15 minutes then transferred to new tubes and counted again in gamma-counter to determine the amount of IgG retained. Membranes were then incubated in 2 ml serum for 15 minutes (×2), transferred to new tubes and counted in gamma-counter after each wash incubation in serum.

The results indicated that a considerable amount of IgG bound onto nitrocellulose membranes by spot blotting was displaced by incubation of the membranes in 1% PVA solution, whereas only a relatively small amount of IgG was displaced from the glass fibre and nylon membranes. Subsequent incubation of the membranes with serum did not displace IgG already blocked by 1% PVA.

3. IgG Binding to Blocked Membranes

Experiments were conducted to determine the effectiveness of various blocking agents on the membranes, and to determine whether the buffer wash cycle has any effect on the blocking agents.

Circular membrane discs (diameter=0.875 cm) were obtained by punching holes through the membranes with an arch punch. The dry membrane discs were soaked in 1 ml solutions of various blocking agents and allowed to equilibrate overnight. The membrane discs were then transferred to new tubes and air-dried for approximately 3 hours before incubating in 1 ml solution containing 200 μg/ml of radiolabelled IgG. Membranes were then washed in Tris-HCl buffer (50 mM, pH 7.4) and counted for gamma-radiation to determine amount of IgG bound. The buffer wash was repeated and the membranes counted again for gamma-radiation. After the second buffer wash, the membranes were re-equilibrated with 1 ml solution containing 200 mg/ml of radiolabelled IgG for 15 minutes. A further buffer wash was done to determine the amount of IgG retained on the membranes.

Results indicated that the amount of IgG bound to blocked membranes was considerably less than the amount bound to membranes that were not blocked, i.e. membranes equilibrated with IgG in Tris-HCl buffer. Except for the glass fibre and nylon membranes, PVA (15,000), PVA (22,000), PVA (49,000) & PVP (40,000) effectively blocked the binding of IgG to all the nitrocellulose membranes (data not shown). The other water soluble polymers, PEG (6,000), PEG (20,000) and Dextran, were not as good blocking agents as PVA and PVP were for all the membranes, except in the case of the glass fibre membrane-A/E (data not shown). Among the neutral detergents (Tween 20, Pluronic P-105, and Triton X-100), Tween 20 appeared to block the nitrocellulose and nylon membranes better than Triton and Pluronic. Furthermore, Triton and Pluronic did not block the glass fibre (A/E) and Nylon membranes (M5 & M10) effectively. BSA generally blocked all the membranes fairly well; however, it was not as effective in blocking the nitrocellulose membranes as PVA and PVP. Re-equilibriating the membranes in IgG indicated that the wash cycles with buffer did not have any effect on the blocking agents used prior to binding IgG (data not shown).

4. Binding of IgG in Serum to Blocked Membranes

Experiments were conducted to determine the amount of IgG bound in the presence of serum to membranes blocked with various blocking agents.

Circular membrane discs (diameter=0.875 cm) were obtained by punching holes through the membranes with an arch punch. The dry membrane discs were soaked in 1 ml solutions of various blocking agents and allowed to equilibrate overnight. The membrane discs were then transferred to new tubes and air-dried for approximately 3 hours before incubating in 1 ml serum containing 200 μg/ml of radiolabelled IgG. The amount of IgG bound to membranes were determined by gamma-count before and after buffer wash. The results indicated that, in the presence of serum, IgG binding to membranes that were pre-blocked with various blocking agent was negligible. Serum acted as a blocking agent as well since the membranes that were not blocked, i.e. those incubated in tris-HCl buffer with serum and radiolabelled IgG, did not bind any appreciable amount of IgG (data not shown).

C. Conditions for Latex Release and Migration

In assays described herein, coated particles are dried into the contact zone of the membrane (and/or the contact pad). Experiments indicated that application of particles either by spraying a suspension with an air brush, or by adding small drops manually, was acceptable.

To examine the conditions for latex release and migration, a 30% sucrose solution in water was applied to an area of membrane and allowed to dry. Latex (0.5% in 15% buffered sucrose) was then added to the same area and dried; the membrane was then dipped in buffer or serum, and migration was allowed to proceed. Although the initial sucrose layer aided re-hydration, it obstructed the migration of latex particles through the membrane strip, especially when serum was used as the release agent.

The most straightforward method of application for experimental purposes was manual addition of the latex suspension with a micropipette. From 0.25 to 2% latex in buffered 15% sucrose is applied directly to the blocked membrane and allowed to dry briefly before migration is initiated.

An Aero-Pro 150 airbrush (Hansa-Technik GmbH, Hamburg, Germany) was assessed as an applicator for latex. Use of the air brush gave an even distribution of latex though the membrane; however, there was no way to quantify the amount of latex suspension applied with the manual apparatus. This approach will work if a metered amount and rate is available for the pressurized air spray. Such a method of distribution is appropriate for large scale applications.

D. Conditions for Latex Migration Arrest

In assays described herein, coated particles migrate by capillary action to the detection region, where they react with detection reagent and are immobilized as detection-reagent-particle complexes, and are subsequently detected.

The conditions for latex migration arrest were investigated. A Sartorius NC8, mylar backed membrane was used. A 10 μl solution of thrombospondin in buffer was dried at the detection zone and the membrane was blocked with 1% PVA (15,000) overnight. Blue 0.29 μm sulphate/aldehyde latex particles (IDC) were coated with different concentrations of antibody and blocked with 1% BSA. Different concentrations of particles, suspended in buffered 15% sucrose, were applied to the contact region. Migration was induced by applying buffer containing various concentrations of thrombospondin to the application point of the membrane. Arrested latex at the detection zone was quantitated by image analysis of magnified video images of the detection zone. The signal used was the total difference in grey levels between the detection zone and the surrounding membrane area.

Figure 3:
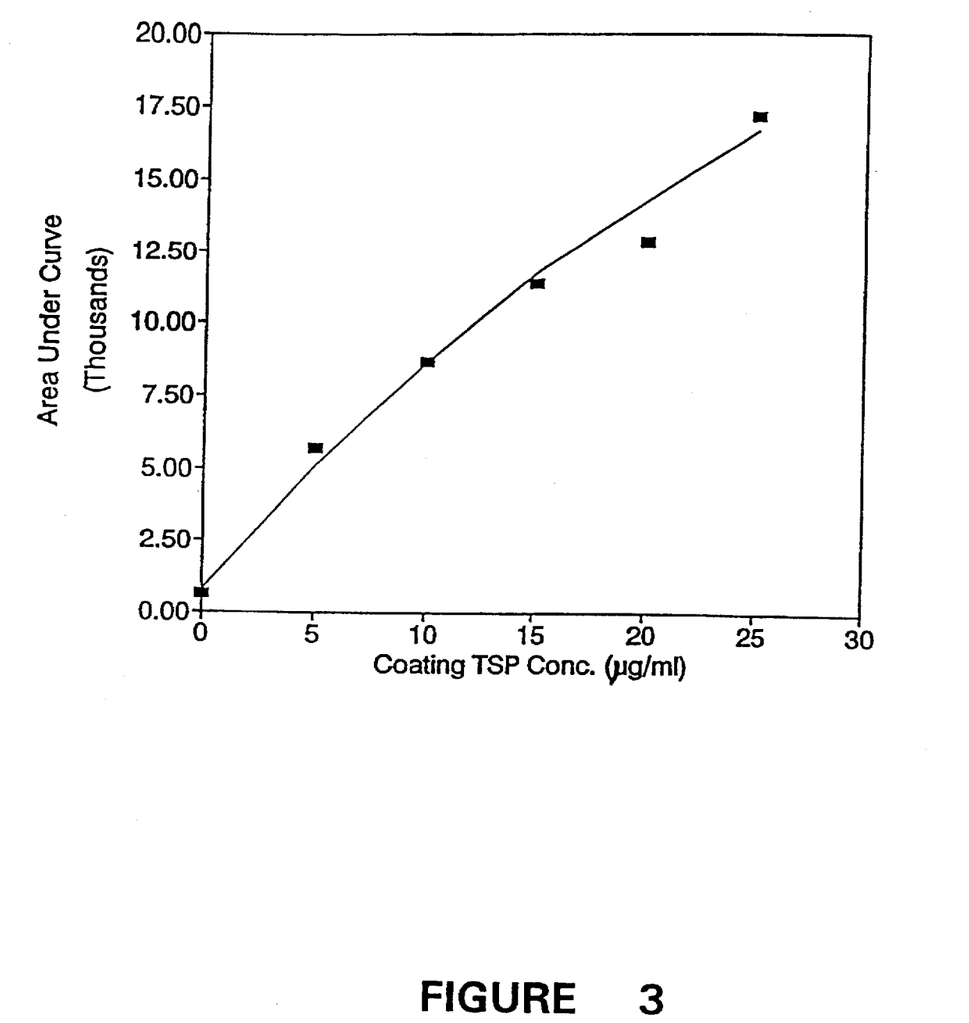
FIG. 3 is a graphic representation of the relationship between the amount of arrested particles in the detection zone and concentration of the detection reagent (thrombospondin). Latex antibody surface concentration, $2 \times 10^{-7}$ g/cm$^2$; latex concentration 2%.
Figure 4:
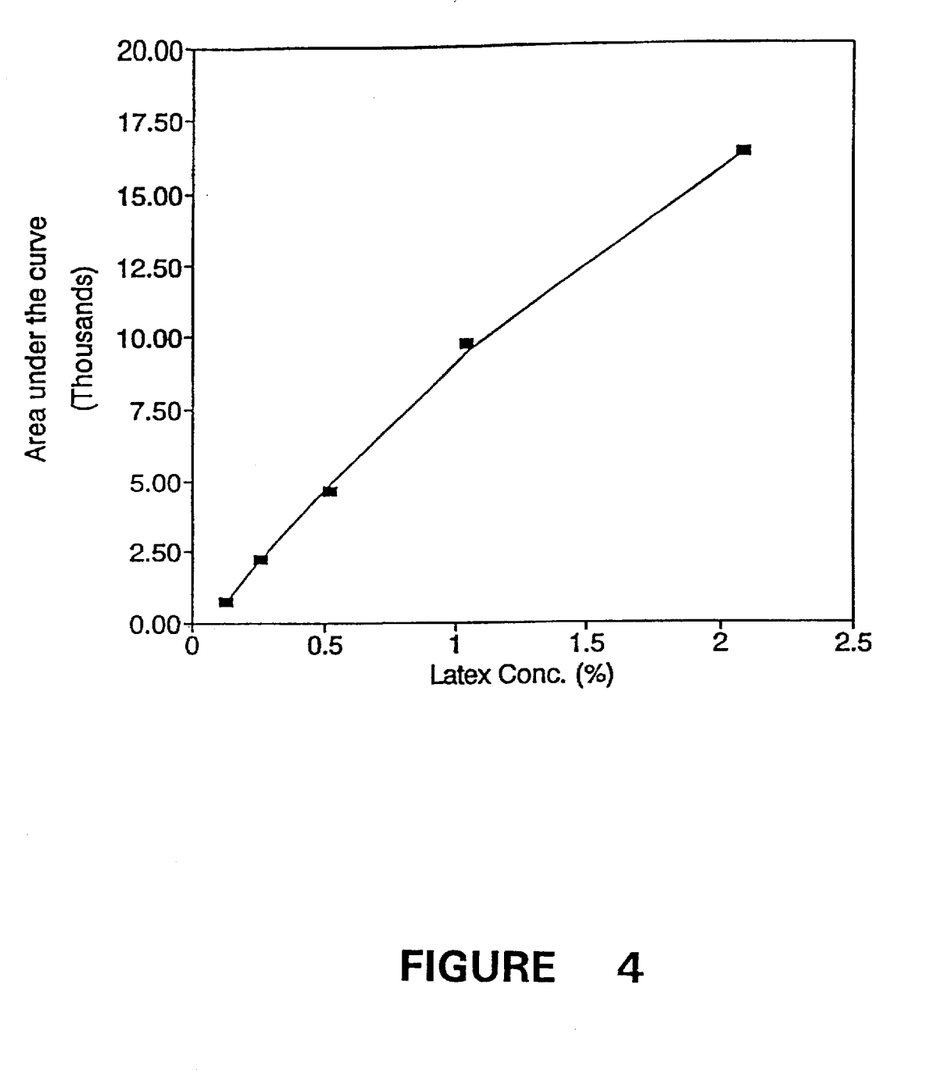
FIG. 4 is a graphic representation of the relationship between the amount of arrested particles in the detection zone and concentration of antibody-coated particles. Latex antibody surface concentration, $2 \times 10^{-7}$ g/cm$^2$; 15 µl of 240 µg/ml thrombospondin on membrane.
Figure 5:
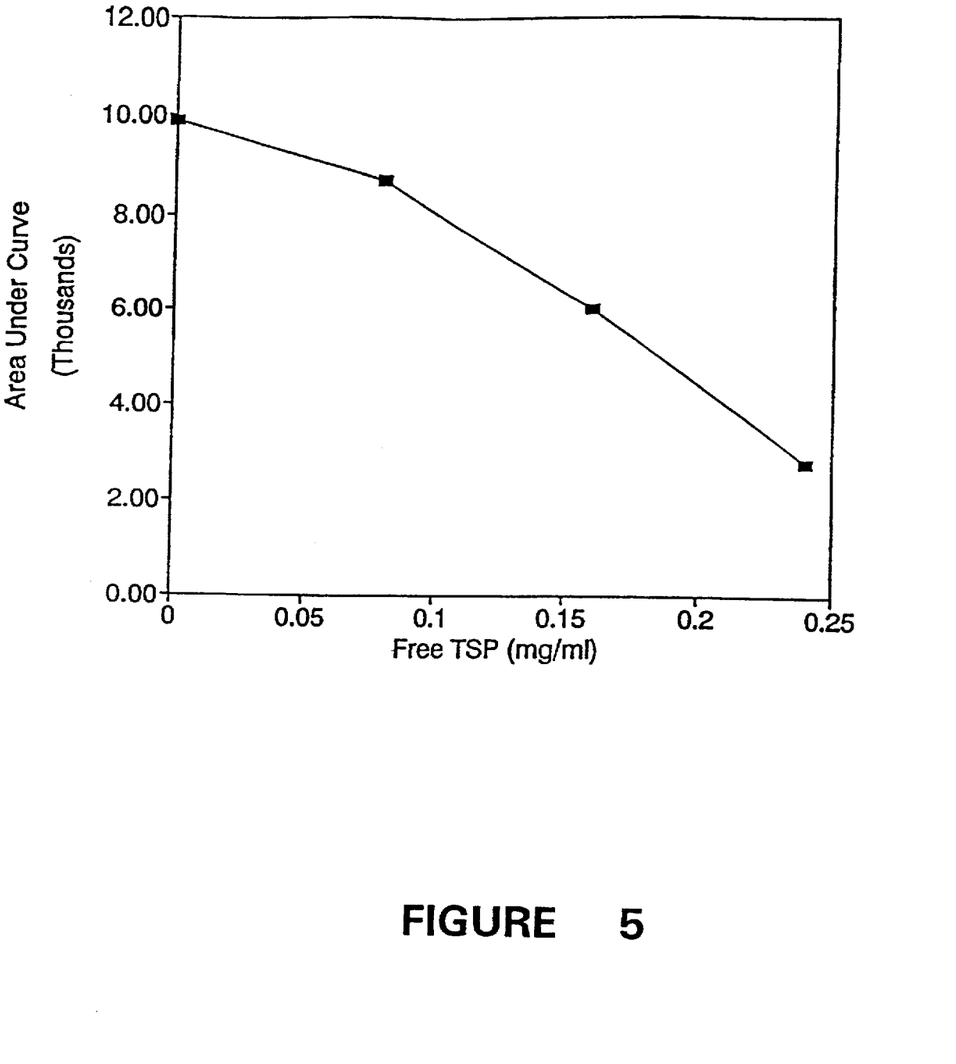
FIG. 5 is a graphic representation of the relationship between the amount of thrombospondin in a fluid sample and the amount of arrested particles in the detection zone. Coating thrombospondin concentration, 240 µg/ml; latex concentration, 0.5%.

The results of these experiments demonstrated that the signal increases approximately linearly with latex antibody surface concentration (FIG. 2), thrombospondin membrane coating concentration (FIG. 3), and latex particle concentration (FIG. 4).

Figure 2:
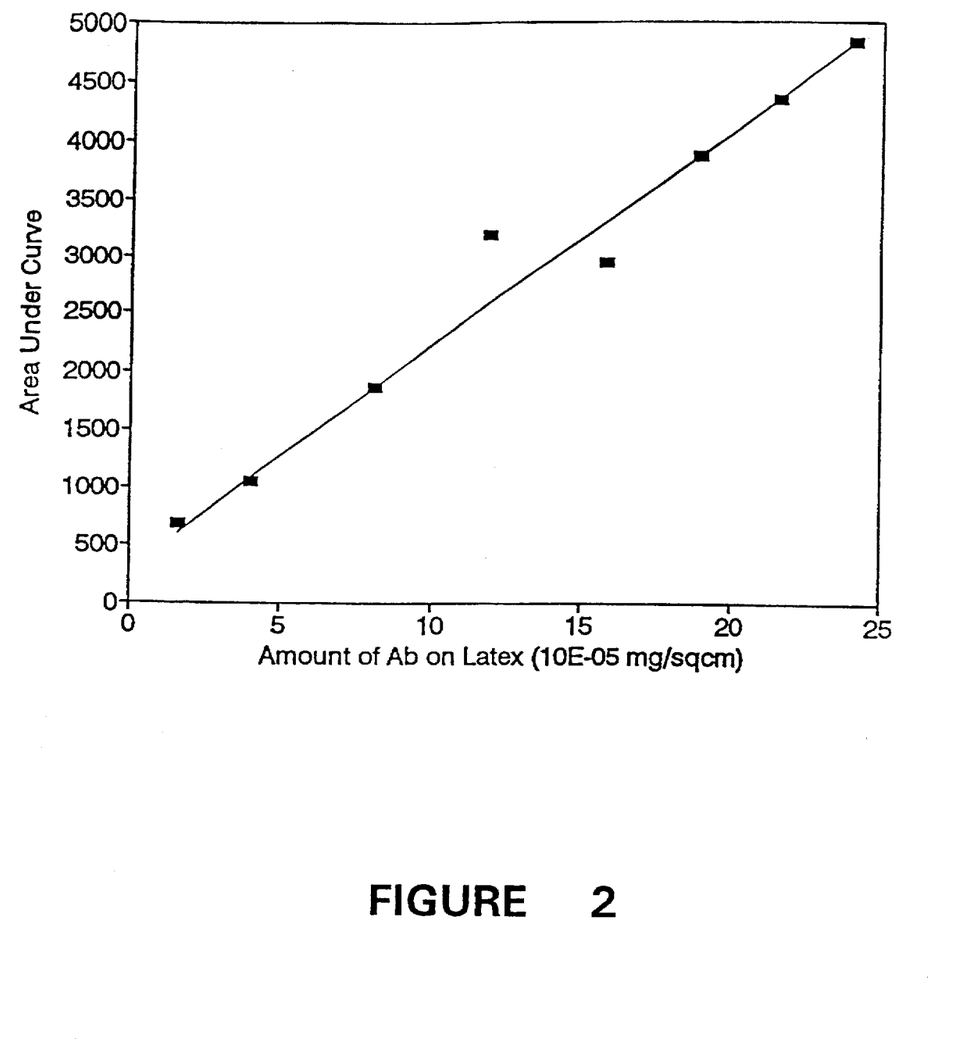
FIG. 2 is a graphic representation of the relationship between the amount of arrested particles in the detection zone and concentration of antibody on the antibody-coated particles. The thrombospondin coating concentration, 240 µg/ml; latex concentration, 0.5%.

Thus, the higher the antibody surface concentration, the greater the number of latex particles arrested in the target region. Furthermore, the number of particles arrested increased strongly with latex concentration, showing only a slight tendency to saturation up to 2% latex. The number of particles arrested increased with increasing thrombospondin concentration in the solution dried into the target area of the membrane, up to about 25 μg/ml thrombospondin. Above this amount, the amount of latex arrested increased little when the thrombospondin concentration increased (e.g., a ten fold increase shown produced only a small increment over the 25 μg/ml value). It was therefore clear that the number of particles arrested in the target zone can be controlled independently by varying the latex number, the surface concentration of antibody on the latex and the thrombospondin concentration dried into the target area.

E. Dependence of Inhibition of Latex Migration Arrest on Free Antigen Concentration In these experiments, latex migration took place by including various concentrations of free thrombospondin in the migration buffer into which one end of the membrane is dipped to produce latex movement. The free thrombospondin inhibits arrest in the target area by competing with antibody binding sites on the latex. The results, shown in FIG. 5, demonstrated that the signal detected in the detection zone was continuously decreased as the concentration of the free antigen in the fluid sample was increased. These results thus demonstrated, both visually and quantitatively, the inhibition of particle arrest by free thrombospondin in a concentration dependent manner.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. A method for quantitatively measuring the amount of an analyte of interest in a sample, comprising the steps of:

a. obtaining a fluid sample to be assayed for the analyte of interest;

b. supplying a rapid antigen measurement platform apparatus, the apparatus comprising a membrane strip, the membrane strip comprising an application point, a contact region, a control reaction zone and a detection zone, wherein the contact region is between the application point and the detection zone;

c. contacting the application point of the membrane strip with the fluid sample;

d. maintaining the membrane strip under conditions which are sufficient to allow fluid to transport analyte of interest in the fluid sample by capillary action through the strip to the contact region, the contact region having a population of antibody-coated particles imbedded therein, wherein the antibody is an antibody to the analyte of interest, and a population of internal control particles imbedded therein, wherein the internal control particles are coated with an antibody to a control detection reagent;

e. further maintaining the membrane strip under conditions which are sufficient to allow analyte of interest to bind to the antibody-coated particles, thereby generating contacted antibody-coated particles; to allow the fluid in the sample to transport the contacted antibody-coated particles by capillary action through the strip to the detection zone, the detection zone having the analyte of interest immobilized thereon, and to allow the fluid in the sample to transport the internal control particles by capillary action through the strip to the control reaction zone, the control reaction zone having the control detection reagent immobilized thereon; to allow the immobilized analyte of interest in the detection zone to bind to contacted antibody-coated particles which are insufficiently coated with the analyte of interest in the fluid sample, and to allow the internal control particles to bind to the control detection reagent; and f. detecting the amount of contacted antibody-coated particles bound to the immobilized analyte of interest in the detection zone, and the amount of internal control particles bound to the control detection reagent in the control reaction zone, wherein the amount of analyte of interest in the fluid sample is inversely related to a ratio of the amount of antibody-coated particles bound to the immobilized analyte of interest in the detection zone, to the amount of internal control particles bound to the control detection reagent in the control reaction zone.

2. The method of claim 1, wherein the membrane strip is made of cellulose nitrate or glass fiber.

3. The method of claim 1, wherein the particles are latex beads.

4. The method of claim 1, wherein the particles are labeled.

5. The method of claim 4, wherein the label is selected from the group consisting of: colorimetric, fluorescent, and luminescent.

6. The method of claim 1, wherein the analyte of interest is thrombospondin, and the fluid sample is blood or a platelet-rich plasma sample.

7. The method of claim 6, wherein the detection reagent is thrombospondin.

8. The method of claim 1, wherein the analyte of interest is myoglobin, and the fluid sample is selected from the group consisting of: whole blood, plasma, and serum.

9. The method of claim 1, wherein the analyte of interest is urinary albumin, and the fluid sample is urine.

10. A method for quantitatively measuring the amount of an analyte of interest in a sample, comprising the steps of:
   a. obtaining a fluid sample to be assayed for the analyte of interest;
   b. supplying a rapid antigen measurement platform apparatus, the apparatus comprising a membrane strip, the membrane strip comprising an application point, a contact region, a control reaction zone and a detection zone, wherein the contact region is between the application point and the detection zone;
   c. contacting the application point of the membrane strip with the fluid sample;
   d. maintaining the membrane strip under conditions which are sufficient to allow fluid to transport analyte of interest in the fluid sample by capillary action through the strip to the contact region, the contact region having a population of antibody-coated particles imbedded therein, wherein the antibody is an antibody to the analyte of interest, and a population of internal control particles imbedded therein, wherein the internal control particles are coated with an antibody to a control detection reagent;
   e. further maintaining the membrane strip under conditions which are sufficient to allow analyte of interest to bind to the antibody-coated particles, thereby generating contacted antibody-coated particles; to allow the fluid in the sample to transport the contacted antibody-coated particles by capillary action through the strip to the detection zone, the detection zone having immobilized thereon an antibody selected from the group consisting of: an antibody directed against the same epitope as the antibody on the antibody-coated particles, and an antibody directed against a different epitope as the antibody on the antibody-coated particles; and to allow the fluid in the sample to transport the internal control particles by capillary action through the strip to the control reaction zone, the control reaction zone having the control detection reagent immobilized thereon; to allow the immobilized antibody in the detection zone to bind to analyte bound to the contacted antibody-coated particles, and to allow the internal control particles to bind to the control detection reagent; and
   f. detecting the amount of contacted antibody-coated particles bound to the immobilized antibody in the detection zone, and the amount of internal control particles bound to the control detection reagent in the control reaction zone, wherein the amount of analyte of interest in the fluid sample is directly related to a ratio of the amount of contacted antibody-coated particles bound to the immobilized antibody in the detection zone, to the amount of internal control particles bound to the control detection reagent in the control reaction zone.

11. The method of claim 10, wherein the membrane strip is made of cellulose nitrate or glass fiber.

12. The method of claim 10, wherein the particles are latex beads.

13. The method of claim 10, wherein the particles are labeled.

14. The method of claim 13, wherein the label is selected from the group consisting of: colorimetric, fluorescent, and luminescent.

15. The method of claim 10, wherein the analyte of interest is thrombospondin, and the fluid sample is blood or a platelet-rich plasma sample.

16. The method of claim 15, wherein the detection reagent is an antibody to thrombospondin.

17. The method of claim 10, wherein the analyte of interest is myoglobin, and the fluid sample is selected from the group consisting of: whole blood, plasma, and serum.

18. The method of claim 10, wherein the analyte of interest is urinary albumin, and the fluid sample is urine.

19. A method for measuring the amount of an analyte of interest in a sample, comprising the steps of:
   a. obtaining a fluid sample to be assayed for the analyte of interest;
   b. supplying a rapid antigen measurement platform apparatus, the apparatus comprising a membrane strip, the membrane strip comprising an application point, a contact region, a control reaction zone and a detection zone, wherein the contact region is between the application point and the detection zone;
   c. contacting the application point of the membrane strip with the fluid sample;
   d. maintaining the membrane strip under conditions which are sufficient to allow fluid to transport analyte of interest in the fluid sample by capillary action through the strip to the contact region, the contact region having a population of particles imbedded therein, wherein the particles are coated with an agent that specifically binds to the analyte, and a population of internal control particles imbedded therein, wherein the internal control particles are coated with an antibody to a control detection reagent;
   e. further maintaining the membrane strip under conditions which are sufficient to allow analyte of interest to bind to the coated particles, thereby generating contacted coated particles; to allow the fluid in the sample to transport the contacted coated particles by capillary action through the strip to the detection zone, the detection zone having a detection reagent immobilized thereon, and to allow the fluid in the sample to transport the internal control particles by capillary action through the strip to the control reaction zone, the control reaction zone having the control detection reagent immobilized thereon; to allow the detection reagent to interact with contacted coated particles, thereby generating arrested detection-reagent-particle complexes; and to allow the internal control particles to bind to the control detection reagent; and
   f. detecting the amount of arrested detection-reagent-particle complexes in the detection zone and the amount of internal control particles bound to the control detection reagent in the control reaction zone, wherein the amount of analyte of interest in the fluid sample is related to a ratio of the amount of arrested detection-reagent-particle complexes in the detection zone, to the amount of internal control particles bound to the control detection reagent in the control reaction zone.

20. A method for measuring the amount of an analyte of interest in a sample, comprising the steps of:

a. obtaining a fluid sample to be assayed for the analyte of interest;

b. supplying a rapid antigen measurement platform apparatus, the apparatus comprising a membrane strip, the membrane strip comprising an application point, a contact region, a control reaction zone and a detection zone, wherein the contact region is between the application point ant the detection zone;

c. contacting the detection zone of the membrane strip with the fluid sample, the detection zone having an antibody to the analyte of interest immobilized thereon, and maintaining the membrane strip under conditions which are sufficient to allow analyte of interest to bind to the antibody in the detection zone, thereby generating immobilized analyte;

d. contacting the application point of the membrane strip with a buffer, and maintaining the membrane strip under conditions which are sufficient 1) to allow buffer to transport a population of antibody-coated particles imbedded in the contact region, wherein the antibody is an antibody to the analyte, by capillary action to the detection zone, and 2) to allow buffer to transport a population of internal control particles imbedded in the contact region, wherein the internal control particles are coated with an agent that specifically binds to a control detection reagent, by capillary action through the strip to the control reaction zone, the control reaction zone having the control detection reagent immobilized thereon;

e. further maintaining the membrane strip under conditions which are sufficient 1) to allow immobilized analyte to interact with the antibody-coated particles, thereby generating immobilized analyte-particle complexes, and 2) to allow the internal control particles to bind to the control detection reagent; and f. detecting the amount of immobilized analyte-particle complexes in the detection zone, and the amount of internal control particles bound to the control detection reagent in the control reaction zone, wherein the amount of analyte of interest in the fluid sample is related to a ratio of the amount of immobilized analyte-particle complexes in the detection zone, to the amount of internal control particles bound to the control detection reagent in the control reaction zone.

21. A method for quantitatively measuring the amount of an analyte of interest in a sample, comprising the steps of:

a. obtaining a fluid sample to be assayed for the analyte of interest;

b. supplying a rapid antigen measurement platform apparatus, the apparatus comprising a membrane strip, the membrane strip comprising an application point, a contact region, a control reaction zone and a detection zone, wherein the contact region is between the application point and the detection zone;

c. contacting the application point of the membrane strip with the fluid sample;

d. maintaining the membrane strip under conditions which are sufficient to allow fluid to transport analyte of interest in the fluid sample by capillary action through the strip to the contact region, the contact region having imbedded therein a population of particles coated with an agent that specifically binds to the analyte of interest, and also imbedded therein a population of internal control particles, wherein the internal control particles are coated with an agent that specifically binds to a control detection reagent;

e. further maintaining the membrane strip under conditions which are sufficient to allow analyte of interest to bind to the particles coated with the agent that specifically binds to the analyte of interest, thereby generating contacted, coated particles; to allow the fluid in the sample to transport the contacted, coated particles by capillary action through the strip to the detection zone, the detection zone having a detection reagent immobilized thereon; to allow the fluid in the sample to transport the internal control particles by capillary action through the strip to the control reaction zone, the control reaction zone having the control detection reagent immobilized thereon; to allow the contacted, coated particles to bind to the detection reagent in the detection zone; and to allow the internal control particles to bind to the control detection reagent; and f. detecting the amount of contacted, coated particles bound to the detection reagent in the detection zone, and the amount of internal control particles bound to the control detection reagent in the control reaction zone, wherein the amount of analyte of interest in the fluid sample is related to a ratio of the amount of contacted, coated particles bound to the detection reagent in the detection zone, to the amount of internal control particles bound to the control detection reagent in the control reaction zone.

* * * * *